United States Patent
Locke et al.

(10) Patent No.: US 10,219,952 B2
(45) Date of Patent: Mar. 5, 2019

(54) SYSTEMS AND METHODS FOR COLLECTING EXUDATES IN REDUCED-PRESSURE THERAPY

(71) Applicant: KCI Licensing, Inc., San Antonio, TX (US)

(72) Inventors: Christopher Brian Locke, Bournemouth (GB); Benjamin A. Pratt, Poole (GB)

(73) Assignee: KCI Licensing, Inc., San Antonio, TX (US)

( * ) Notice: Subject to any disclaimer, the term of this patent is extended or adjusted under 35 U.S.C. 154(b) by 1052 days.

(21) Appl. No.: 14/023,870

(22) Filed: Sep. 11, 2013

(65) Prior Publication Data

US 2014/0074053 A1 Mar. 13, 2014

Related U.S. Application Data

(60) Provisional application No. 61/700,217, filed on Sep. 12, 2012.

(51) Int. Cl.
*A61F 13/00* (2006.01)
*A61M 1/00* (2006.01)

(52) U.S. Cl.
CPC ..... *A61F 13/00068* (2013.01); *A61M 1/0052* (2014.02); *A61M 1/0088* (2013.01); *Y10T 29/49826* (2015.01); *Y10T 156/10* (2015.01)

(58) Field of Classification Search
CPC ................. A61F 13/00068; A61M 1/0001
See application file for complete search history.

(56) References Cited

U.S. PATENT DOCUMENTS

| 1,355,846 A | 10/1920 | Rannells |
| 2,547,758 A | 4/1951 | Keeling |
| 2,632,443 A | 3/1953 | Lesher |
| 2,682,873 A | 7/1954 | Evans et al. |
| 2,910,763 A | 11/1959 | Lauterbach |

(Continued)

FOREIGN PATENT DOCUMENTS

| AU | 550575 A1 | 3/1986 |
| AU | 745271 | 4/1999 |

(Continued)

OTHER PUBLICATIONS

Partial International Search Report for corresponding PCT/US2013/059270 dated Jan. 3, 2014.

(Continued)

*Primary Examiner* — Tatyana Zalukaeva
*Assistant Examiner* — Guy K Townsend

(57) ABSTRACT

In one example embodiment, a dressing connector is described that provides a first fluid path between a first connector and a second connector, and a second fluid path between a third connector and a fourth connector. A liquid barrier may be disposed in the first fluid path. The first fluid path and the second fluid path are generally exposed to an exterior surface of the dressing connector. In some embodiments, a tube may also be bonded to the third connector to provide a third fluid path between the dressing connector and another component. In more particular embodiments, the liquid barrier may be a filter, such as a hydrophobic bacterial filter, a sintered polymer filter, and/or a charcoal filter.

22 Claims, 9 Drawing Sheets

(56) References Cited

U.S. PATENT DOCUMENTS

| | | |
|---|---|---|
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielson |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Cation |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2002/0198504 A1* | 12/2002 | Risk, Jr. .............. A61M 1/0058 604/318 |
| 2007/0219532 A1* | 9/2007 | Karpowicz ......... A61M 1/0031 604/540 |
| 2009/0240218 A1* | 9/2009 | Braga ................. A61M 1/0001 604/313 |
| 2009/0292263 A1* | 11/2009 | Hudspeth ............ A61M 1/0001 604/313 |
| 2009/0306630 A1* | 12/2009 | Locke ................. A61M 1/0001 604/543 |
| 2010/0016816 A1* | 1/2010 | Schuessler ......... A61M 1/0023 604/313 |
| 2010/0030132 A1* | 2/2010 | Niezgoda ............ A61M 1/0088 604/22 |
| 2010/0042074 A1* | 2/2010 | Weston ............... A61M 1/0066 604/543 |
| 2010/0069886 A1* | 3/2010 | Wilkes ................ A61M 1/0084 604/543 |
| 2010/0106184 A1* | 4/2010 | Coward .............. A61M 1/0088 606/213 |
| 2010/0150991 A1* | 6/2010 | Bernstein ............... A61K 31/00 424/447 |
| 2010/0179493 A1* | 7/2010 | Heagle ................ A61M 1/0001 604/313 |
| 2010/0204663 A1* | 8/2010 | Wudyka .............. A61M 1/0088 604/313 |
| 2010/0262094 A1* | 10/2010 | Walton ............... A61M 1/0023 604/319 |
| 2010/0318043 A1* | 12/2010 | Malhi ................. A61M 1/0001 604/313 |
| 2011/0077605 A1* | 3/2011 | Karpowicz ......... A61M 1/0001 604/318 |
| 2011/0106027 A1* | 5/2011 | Vess .................... A61M 1/0023 604/319 |
| 2011/0224633 A1* | 9/2011 | Robinson ............ A61M 1/0031 604/319 |
| 2011/0251569 A1* | 10/2011 | Turner ................ A61M 1/0005 604/318 |
| 2012/0123358 A1* | 5/2012 | Hall .................... A61M 1/0088 604/318 |
| 2012/0136325 A1* | 5/2012 | Allen .................. A61M 1/0031 604/319 |
| 2012/0310189 A1* | 12/2012 | Wang .................. A61M 1/0088 604/319 |
| 2013/0053797 A1* | 2/2013 | Locke ................. A61M 1/0088 604/319 |
| 2013/0110058 A1* | 5/2013 | Adie ................... A61M 1/0031 604/319 |
| 2013/0131616 A1* | 5/2013 | Locke ................. A61M 1/0031 604/321 |

(56) References Cited

U.S. PATENT DOCUMENTS

| | | | | |
|---|---|---|---|---|
| 2013/0165821 A1* | 6/2013 | Freedman | ......... | A61F 13/00063 601/2 |
| 2013/0296816 A1* | 11/2013 | Greener | .............. | A61M 1/0031 604/320 |
| 2014/0074053 A1* | 3/2014 | Locke | ............... | A61F 13/00068 604/319 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 4/2002 |
| WO | 80/02182 | 10/1980 |
| WO | 87/04626 | 8/1987 |
| WO | 90/010424 | 9/1990 |
| WO | 93/09727 | 5/1993 |
| WO | 94/020041 | 9/1994 |
| WO | 96/05873 | 2/1996 |
| WO | 97/18007 | 5/1997 |
| WO | 99/13793 | 3/1999 |
| WO | 2009019496 A2 | 2/2009 |
| WO | 2009149250 A1 | 12/2009 |

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (copy and certified translation).
Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Ðukić, Ž. Maksimović, Ð. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its

(56) References Cited

OTHER PUBLICATIONS

Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians (Jul. 2007).

Examination Report for corresponding European Application No. EP13773908.2 dated Jul. 21, 2016.

\* cited by examiner

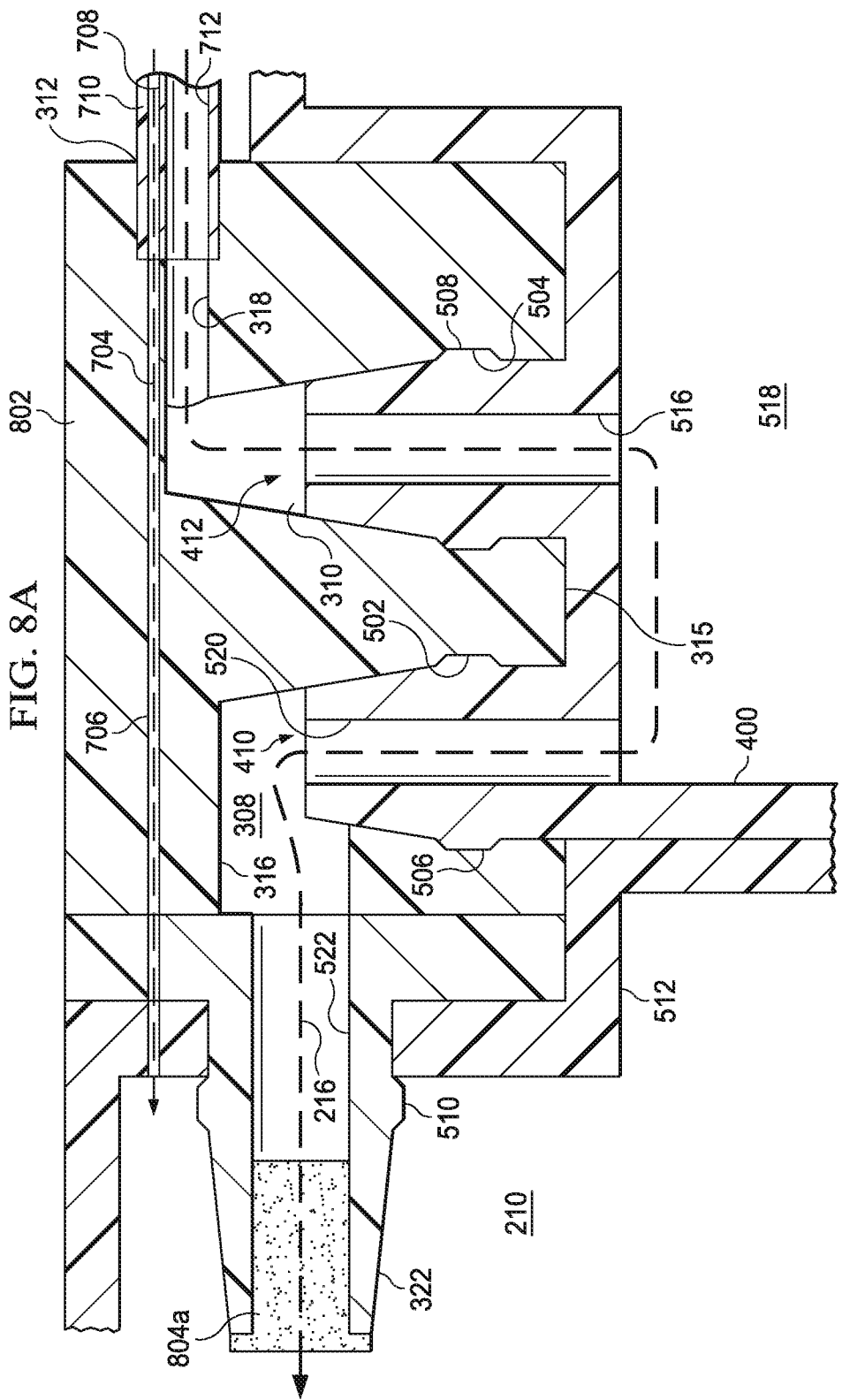

SYSTEMS AND METHODS FOR COLLECTING EXUDATES IN REDUCED-PRESSURE THERAPY

RELATED APPLICATION

The present invention claims the benefit, under 35 USC § 119(e), of the filing of U.S. Provisional Patent Application Ser. No. 61/700,217, entitled "SYSTEMS AND METHODS FOR COLLECTING EXUDATES IN REDUCED-PRESSURE THERAPY," filed 12 Sep. 2012, which is incorporated herein by reference for all purposes.

BACKGROUND

The present invention relates generally to tissue treatment systems and more particularly to systems and methods for collecting exudates in reduced-pressure therapy.

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds with reduced pressure may be commonly referred to as "reduced-pressure wound therapy," but is also known by other names, including "negative-pressure therapy," negative-pressure wound therapy," and "vacuum therapy," for example Reduced-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of reduced-pressure therapy are widely known, the cost and complexity of reduced-pressure therapy can be a limiting factor in its application, and the development and operation of reduced-pressure systems, components, and processes continues to present significant challenges to manufacturers, healthcare providers, and patients.

BRIEF SUMMARY

In one example embodiment, a dressing connector is described herein that provides a first fluid path between a first connector and a second connector, and a second fluid path between a third connector and a fourth connector. A liquid barrier may be disposed in the first fluid path. The first fluid path and the second fluid path are generally exposed to an exterior surface of the dressing connector. In certain embodiments, the first connector may be a fitting, the second connector may be a receptacle, the third connector may be a port, and the fourth connector may be another receptacle. In some embodiments, a tube may also be bonded to the third connector to provide a third fluid path between the dressing connector and another component. In more particular embodiments, the liquid barrier may be a filter, such as a hydrophobic bacterial filter, a gel-blocking sintered polymer filter, and/or a charcoal filter.

Alternatively, an example embodiment may provide a fitting fluidly coupled to a first receptacle through an inline liquid barrier, a port fluidly coupled to a second receptacle, and a tube fluidly coupled to the port. The fitting may be adapted to engage a downstream component, such as a reduced-pressure source. The first receptacle and the second receptacle each may provide a cavity exposed to an exterior surface adapted to engage a container fitting.

A reduced-pressure treatment system is also described herein, wherein one example embodiment includes a downstream component, such as a reduced-pressure source, a reusable container, and a disposable dressing connector. The dressing connector may be coupled to the container and to an upstream component, such as a dressing. The dressing connector provides a first fluid path between the downstream component and the container, and a second fluid path between the container and the upstream component. A liquid barrier can be disposed in the first fluid path between the container and the downstream component. In some embodiments, a tube may couple the dressing connector to the downstream component, the upstream component, or both.

A method of manufacturing a dressing component is also described herein, wherein one example embodiment includes forming a first interface comprising a first port, a second port, a first receptacle, and a second receptacle. A first channel may be formed from the first port to the first receptacle. A second channel may be formed from the second port to the second receptacle. A tube may be coupled to the first port, such as by bonding the tube to the first port with an adhesive. A second interface may be formed with a third port and a fitting. The second port and the third port may be aligned and a liquid barrier disposed between the second port and the third port before coupling the first interface to the second interface.

A method of operating a reduced-pressure system to provide reduced-pressure therapy is also described. In one example method of providing reduced-pressure therapy, a dressing may be coupled to a first dressing connector. For example, a dressing may be applied to a tissue site and a tube may be coupled to the dressing and to the first dressing connector. The first dressing connector may then be coupled to a reusable fluid container, such as by pressing receptacles of the first dressing connector onto fittings of the fluid container. In some embodiments, orientation recesses of the first dressing connector may also be aligned with corresponding orientation fittings on the fluid container. The fluid container and the first dressing connector can then be coupled to a reduced-pressure source or other downstream component, such that a liquid barrier in the first dressing connector can be positioned between the fluid container and the reduced-pressure source. Reduced pressure can be applied to a tissue site through the dressing.

Reduced-pressure may be applied and exudates collected from the tissue site in the fluid container. Exudates may be emptied from the fluid container and the first dressing connector may be replaced with a second dressing connector having a second (and preferably unused) liquid barrier. The first dressing connector can be disposed of with the dressing, which encourages regular changes of liquid barriers.

Other objects, features, and advantages of the embodiments described herein will become apparent with reference to the drawings and detailed description that follow.

BRIEF DESCRIPTION OF THE DRAWINGS

FIGS. 8A-8B are partial cross-sectional views of yet other example embodiments of a dressing connector engaged with a canister that may be associated with the reduced-pressure therapy system.

DESCRIPTION OF EXAMPLE EMBODIMENTS

New and useful systems and methods for collecting exudates in a reduced-pressure therapy environment are set forth in the appended claims. Objectives, advantages, and a preferred mode of making and using the systems and methods may be understood best by reference to the following detailed description in conjunction with the accompanying drawings. The description provides information that enables a person skilled in the art to make and use the claimed subject matter, but may omit certain details already well-known in the art. Moreover, descriptions of various alternatives using terms such as "or" do not necessarily require mutual exclusivity unless clearly required by the context. The claimed subject matter may also encompass alternative embodiments not specifically described in detail. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1A:
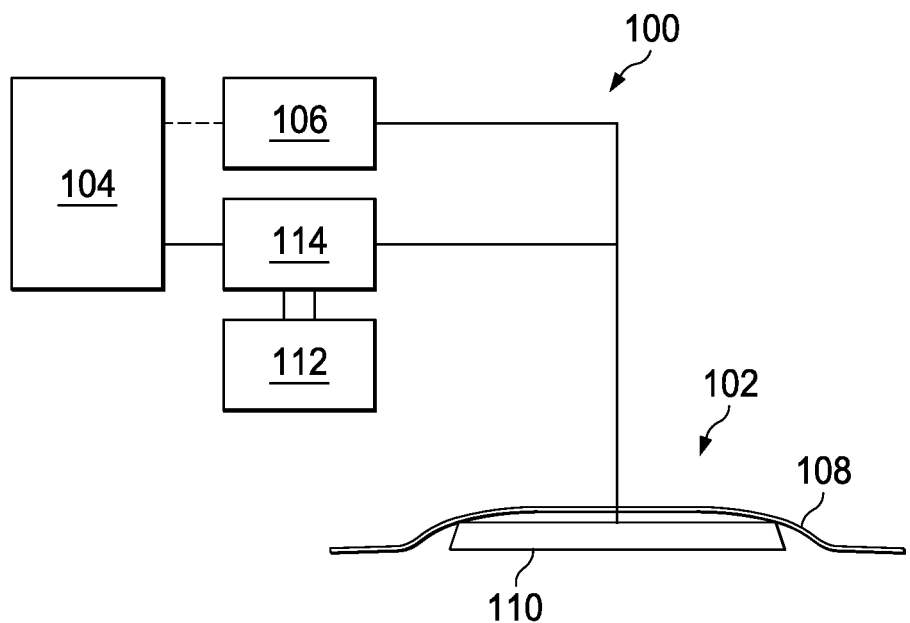
FIGS. 1A-1B are functional block diagrams of example embodiments of a reduced-pressure therapy system that can collect exudates in accordance with this specification.
Figure 1B:
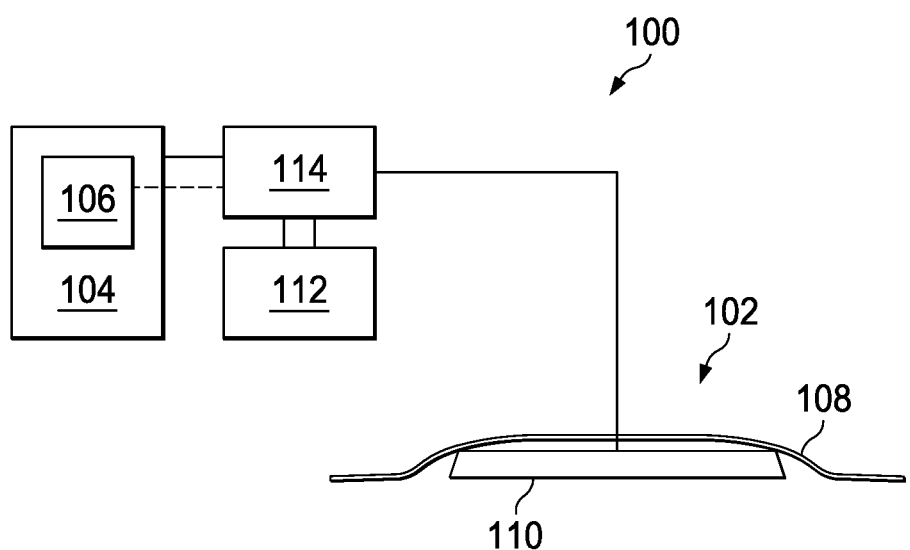

FIGS. 1A-1B are simplified functional block diagrams of example embodiments of a reduced-pressure therapy system 100 that can collect exudates in accordance with this specification. As illustrated, reduced-pressure therapy system 100 may include a dressing 102 fluidly coupled to a reduced-pressure source 104. A regulator or controller, such as regulator 106, may also be fluidly coupled to dressing 102 and reduced-pressure source 104. Dressing 102 generally includes a drape, such as drape 108, and a manifold, such as pressure distribution manifold 110. Reduced-pressure therapy system 100 may also include fluid container, such as container 112, coupled to dressing 102 and reduced-pressure source 104.

In general, components of reduced-pressure therapy system 100 may be coupled directly or indirectly. For example, reduced-pressure source 104 may be directly coupled to regulator 106 and indirectly coupled to dressing 102 through regulator 106. Components may be fluidly coupled to each other to provide a path for transferring fluids (i.e., liquid and/or gas) between the components. In some embodiments, components may be fluidly coupled with a tube, for example. A "tube," as used herein, broadly refers to a tube, pipe, hose, conduit, or other structure with one or more lumina adapted to convey fluids between two ends. Typically, a tube is an elongated, cylindrical structure with some flexibility, but the geometry and rigidity may vary. In some embodiments, components may additionally or alternatively be coupled by virtue of physical proximity, being integral to a single structure, or being formed from the same piece of material. Coupling may also include mechanical, thermal, electrical, or chemical coupling (such as a chemical bond) in some contexts.

In operation, pressure distribution manifold 110 may be placed within, over, on, or otherwise proximate to a tissue site. Drape 108 may be placed over pressure distribution manifold 110 and sealed to tissue proximate the tissue site. The tissue proximate to the tissue site is often undamaged epidermis peripheral to the tissue site. Thus, dressing 102 can provide a sealed therapeutic environment proximate to a tissue site, substantially isolated from the external environment, and reduced-pressure source 104 can reduce the pressure in the sealed therapeutic environment. Reduced pressure applied uniformly through pressure distribution manifold 110 in the sealed therapeutic environment can induce macrostrain and microstrain in the tissue site, as well as remove exudates and other fluids from the tissue site, which can be collected in container 112 and disposed of properly.

The fluid mechanics of using a reduced-pressure source to reduce pressure in another component or location, such as within a sealed therapeutic environment, can be mathematically complex. However, the basic principles of fluid mechanics applicable to reduced-pressure therapy are generally well-known to those skilled in the art, and the process of reducing pressure may be described illustratively herein as "delivering," "distributing," or "generating" reduced pressure, for example.

In general, exudates and other fluids flow toward lower pressure along a fluid path. This orientation is generally presumed for purposes of describing various features and components of reduced-pressure therapy systems herein. Thus, the term "downstream" typically implies something in a fluid path relatively closer to a reduced-pressure source, and conversely, the term "upstream" implies something relatively further away from a reduced-pressure source. Similarly, it may be convenient to describe certain features in terms of fluid "inlet" or "outlet" in such a frame of reference. However, the fluid path may also be reversed in some applications (such as by substituting a positive-pressure source for a reduced-pressure source) and this descriptive convention should not be construed as a limiting convention.

The term "tissue site" in this context broadly refers to a wound or defect located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, reduced pressure may be used in certain tissue areas to grow additional tissue that may be harvested and transplanted to another tissue location.

"Reduced pressure" generally refers to a pressure less than a local ambient pressure, such as the ambient pressure in a local environment external to a sealed therapeutic environment provided by dressing 102. In many cases, the local ambient pressure may also be the atmospheric pressure at which a patient is located. Alternatively, the pressure may be less than a hydrostatic pressure associated with tissue at the tissue site. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

A reduced-pressure source, such as reduced-pressure source 104, may be a reservoir of air at a reduced pressure, or may be a manual or electrically-powered device that can reduced the pressure in a sealed volume, such as a vacuum pump, a suction pump, a wall suction port available at many healthcare facilities, or a micro-pump, for example. The reduced-pressure source may be housed within or used in conjunction with other components, such as sensors, processing units, alarm indicators, memory, databases, software, display devices, or user interfaces that further facilitate reduced-pressure therapy. While the amount and nature of reduced pressure applied to a tissue site may vary according to therapeutic requirements, the pressure typically ranges between −5 mm Hg (−667 Pa) and −500 mm Hg (−66.7 kPa). Common therapeutic ranges are between −75 mm Hg (−9.9 kPa) and −300 mm Hg (−39.9 kPa).

Pressure distribution manifold 110 can be generally adapted to contact a tissue site. Pressure distribution manifold 110 may be partially or fully in contact with the tissue site. If the tissue site is a wound, for example, pressure distribution manifold 110 may partially or completely fill the wound, or may be placed over the wound. Pressure distribution manifold 110 may take many forms, and may have many sizes, shapes, or thicknesses depending on a variety of factors, such as the type of treatment being implemented or the nature and size of a tissue site. For example, the size and shape of pressure distribution manifold 110 may be adapted to the contours of deep and irregular shaped tissue sites.

More generally, a manifold is a substance or structure adapted to distribute reduced pressure to and/or remove fluids from a tissue site, or both. In some embodiments, though, a manifold may also facilitate delivering fluids to a tissue site, if the fluid path is reversed or a secondary fluid path is provided, for example. A manifold may include flow channels or pathways that distribute fluids provided to and removed from a tissue site around the manifold. In one illustrative embodiment, the flow channels or pathways may be interconnected to improve distribution of fluids provided to or removed from a tissue site. For example, cellular foam, open-cell foam, porous tissue collections, and other porous material such as gauze or felted mat generally include structural elements arranged to form flow channels. Liquids, gels, and other foams may also include or be cured to include flow channels.

In one illustrative embodiment, pressure distribution manifold 110 may be a porous foam material having interconnected cells or pores adapted to uniformly (or quasi-uniformly) distribute reduced pressure to a tissue site. The foam material may be either hydrophobic or hydrophilic. In one non-limiting example, pressure distribution manifold 110 can be an open-cell, reticulated polyurethane foam such as GranuFoam® dressing available from Kinetic Concepts, Inc. of San Antonio, Tex.

In an example in which pressure distribution manifold 110 may be made from a hydrophilic material, pressure distribution manifold 110 may also wick fluid away from a tissue site, while continuing to distribute reduced pressure to the tissue site. The wicking properties of pressure distribution manifold 110 may draw fluid away from a tissue site by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

Pressure distribution manifold 110 may further promote granulation at a tissue site when pressure within the sealed therapeutic environment is reduced. For example, any or all of the surfaces of pressure distribution manifold 110 may have an uneven, coarse, or jagged profile that can induce microstrains and stresses at a tissue site if reduced pressure is applied through pressure distribution manifold 110.

In one embodiment, pressure distribution manifold 110 may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. Pressure distribution manifold 110 may further serve as a scaffold for new cell-growth, or a scaffold material may be used in conjunction with pressure distribution manifold 110 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

Drape 108 is an example of a sealing member. A sealing member may be constructed from a material that can provide a fluid seal between two components or two environments, such as between a therapeutic environment and a local external environment. The sealing member may be, for example, an impermeable or semi-permeable, elastomeric material that can provide a seal adequate to maintain a reduced pressure at a tissue site for a given reduced-pressure source. For semi-permeable materials, the permeability generally should be low enough that a desired reduced pressure may be maintained. An attachment device may be used to attach a sealing member to an attachment surface, such as undamaged epidermis, a gasket, or another sealing member. The attachment device may take many forms. For example, an attachment device may be a medically-acceptable, pressure-sensitive adhesive that extends about a periphery, a portion, or an entire sealing member. Other example embodiments of an attachment device may include a double-sided tape, paste, hydrocolloid, hydrogel, silicone gel, organogel, or an acrylic adhesive.

Container 112 is representative of a container, canister, pouch, or other storage component that can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with reduced-pressure therapy. Liquid barriers are usually an integral part of most reduced-pressure therapy containers, though. For example, certain filters can reduce odor and prevent exudates from entering the reduced-pressure source and other components downstream from the container. In general, liquid barriers allow air to flow from the container to the reduced-pressure source while preventing contamination. However, protein deposits can accumulate on the liquid barriers and gradually reduce the volume of air flowing from the container, which can adversely affect therapy and cause false blockage alarms. Consequently, filters can be a limiting factor for re-using a container.

As disclosed herein, reduced-pressure therapy system 100 can overcome these shortcomings and others by providing a re-usable container for collecting exudates that ensures filter changes at regular intervals. For example, in some embodiments of reduced-pressure therapy system 100, container 112 may be a re-usable fluid container, and a single-use dressing connector, such as connector 114, may couple container 112 to dressing 102 and reduced-pressure source 104. In one particular embodiment, the dressing connector includes an integrated, inline liquid barrier and provides two pneumatic pathways. In general, the first pneumatic pathway can connect the dressing to the fluid container, and the second pneumatic pathway can connect the fluid container to the reduced-pressure source or other downstream components, through the liquid barrier. The dressing connector may also include a tube having one end bonded or semi-permanently coupled to the first pneumatic pathway. The other end of the tube can be connected to the dressing during therapy. In some embodiments, the second pneumatic pathway may be directly coupled to a reduced-pressure source through a port adapted for mating with the reduced-pressure source, while in other embodiments the second pneumatic pathway may be indirectly coupled to a reduced-pressure source through one or more intermediate components. The fluid container may also include a drain port with a drain cover that may be removed and replaced. The fluid container may be a rigid canister in some embodiments, but may be a flexible container such as a soft-sided pouch in other embodiments.

In general, reduced-pressure therapy may be applied until a dressing requires replacement or therapy is complete. When the dressing requires replacement or therapy is complete, the fluid container may be emptied and the dressing connector (with the integrated liquid barrier) can be disposed of with the dressing. Consequently, the liquid barrier may only be used for a fixed duration or for a fixed volume of exudates, which substantially reduces or eliminates cross-contamination between patients (as a dressing should not be used on multiple patients) and blockages due to extended use by a single patient.

Figure 2:
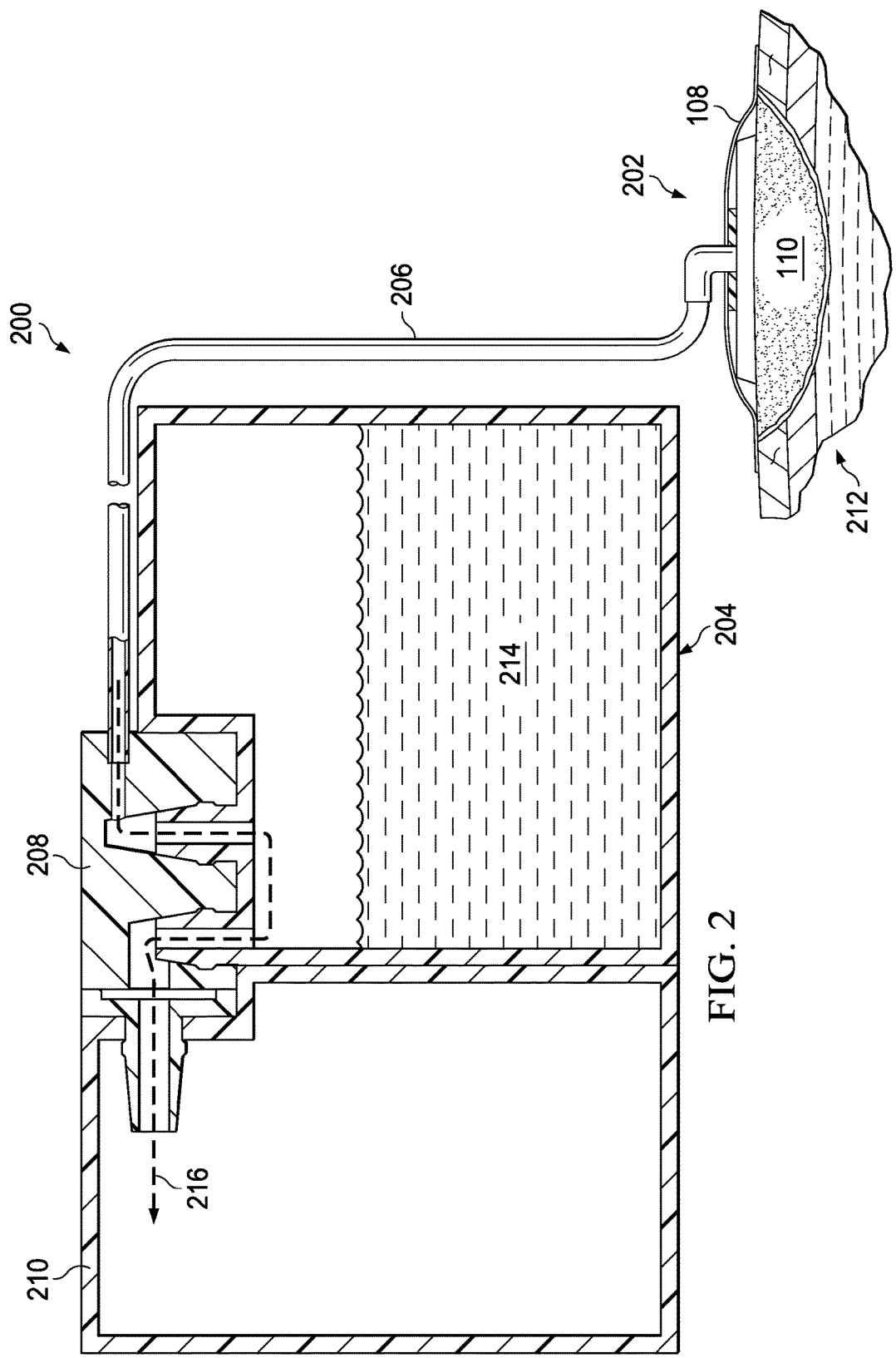
FIG. 2 is a schematic diagram illustrating additional details that may be associated with an example embodiment of the reduced-pressure therapy system.

FIG. 2 is a schematic diagram illustrating additional details that may be associated with an example embodiment of reduced-pressure therapy system 100. In this example embodiment, reduced-pressure therapy system 100 generally includes a dressing 202 fluidly coupled to a container, such as canister 204, through a tube 206 and dressing connector 208. In some embodiments, a dressing interface (not shown) may facilitate coupling dressing 202 and tube 206. For example, such a dressing interface may be a T.R.A.C.® Pad or Sensa T.R.A.C.® Pad available from KCI of San Antonio, Tex. In some embodiments, the dressing interface may be a portion of tube 206 extending into the sealed therapeutic environment, or may be a vacuum port on a micro-pump that extends into the sealed therapeutic environment.

Dressing connector 208 in this example embodiment can be directly coupled to a reduced-pressure source 210. Thus, canister 204 can be fluidly coupled to both dressing 202 and reduced-pressure source 210. Canister 204 and reduced-pressure source 210 may additionally be mechanically coupled to increase stability, such as with a fastener or interlocking features. As illustrated in FIG. 2, dressing 202 may be applied to a tissue site 212, and exudates 214 may be removed from the tissue site 212 and collected in canister 204 as reduced-pressure therapy is applied. In general, exudates and other fluids flow toward lower pressure along a fluid path 216.

Figure 3:
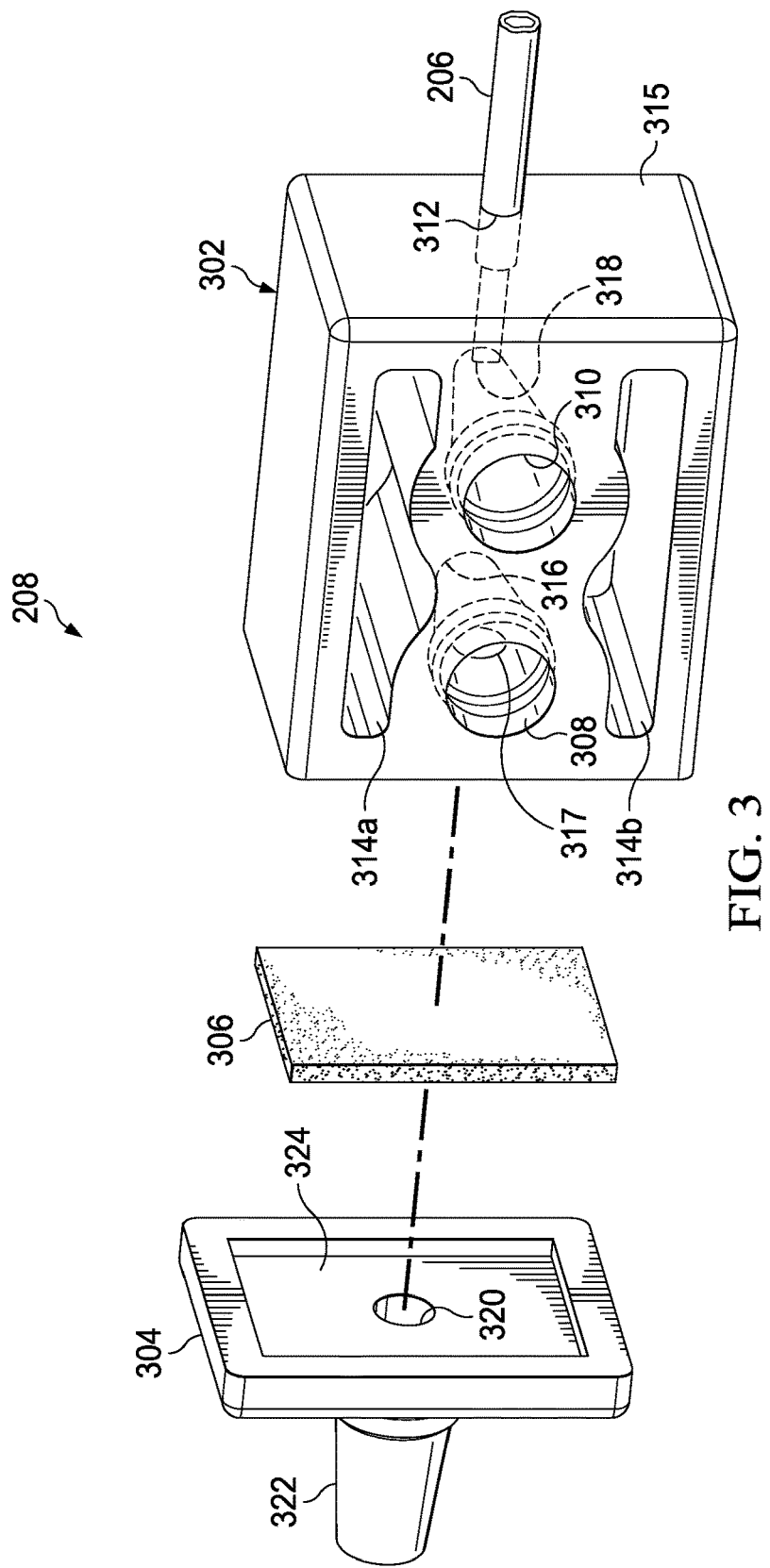
FIG. 3 is an exploded diagram illustrating additional details that may be associated with an example embodiment of a dressing connector that may be associated with the reduced-pressure therapy system.

FIG. 3 is an exploded diagram illustrating additional details that may be associated with an example embodiment of dressing connector 208. In this example embodiment, dressing connector 208 generally includes interfaces 302-304 and a liquid barrier 306. Interface 302 may be generally described as a "container interface" that provides connectors, fasteners, or fittings adapted to mate with corresponding connectors, fasteners, or fittings of another component, particularly a fluid container. In FIG. 3, for example, interface 302 is illustrated with three female connectors, i.e., receptacles 308-310 and a port 312, but other combinations of male and female connectors are also possible. Interface 302 may additionally provide one or more orientation guides, such as orientation recesses 314a-314b. Receptacles 308-310, port 312, and orientation recesses 314a-314b are generally exposed to an exterior surface 315 of dressing connector 208. For example, in the example embodiment of FIG. 3, receptacles 308-310 are exposed on a first side of exterior surface 315 and port 312 is exposed on a second, adjacent side.

In more particular embodiments, receptacles 308-310 may be generally described as cavities exposed to exterior surface 315 and adapted to receive and hold a male connector. In yet more particular embodiments, receptacle 308 may be an inlet receptacle adapted to receive fluid flow from an outlet fitting of a container, and receptacle 310 may be an outlet receptacle adapted to exhaust fluid flow into the container. A channel 316 may fluidly couple receptacle 308 to an aperture 317, and a channel 318 may fluidly couple receptacle 310 to port 312. Tube 206 may be bonded or semi-permanently attached to port 312 to prevent separation under expected therapeutic conditions. For example, tube 206 may be bonded to port 312 with an adhesive, glue, or cement, or tube 206 and port 312 may be sized to provide a press fit.

Interface 304 may be generally described as a "downstream interface" that provides an aperture 320 adapted for fluid communication with channel 316 and a connector adapted to engage a downstream component. In FIG. 3, for example, the connector is represented as a fitting 322 that may be adapted to mechanically couple with reduced-pressure source 210. In the illustrated embodiment, fitting 322 is a male fitting (i.e., a part bearing one or more protrusions) adapted to engage a female fitting or receptacle, but in other embodiments, fitting 322 may be a female fitting adapted to engage a male fitting, for example. Interface 304 may additionally include a recess 324 adapted to receive liquid barrier 306.

In this example embodiment, tube 206 can be fluidly coupled to port 312 (i.e., through a lumen in tube 206) and port 312 can be fluidly coupled to receptacle 310 (i.e., through channel 318). When assembled, aperture 320 may be aligned with aperture 317 to fluidly couple fitting 322 to receptacle 316 through liquid barrier 306.

In more particular embodiments, liquid barrier 306 may be a hydrophobic, bacterial filter. A charcoal filter may also be co-located or placed inline with the hydrophobic, bacterial filter to reduce odor. In yet more particular embodiments, liquid barrier 306 may be a gel-blocking sintered polymer filter that swells on contact with water, which can block the fluid path between a reduced-pressure source and a canister. Suitable polymers include, for example, fluoropolymers such as polytetrafluoroethylene (PTFE), polyvinylidene fluoride (PVdF), or fluorinated ethylenepropylene (FEP); chlorofluoropolymers, such as polychlorotrifluoroethylene (PCTFE); polyolefins such as high density polyethylene (HDPE), polypropylene (PP), cyclic olefin copolymer (COC), or polymethylpent-1-ene (PMP); polyvinyl acetate (PVAc) or ethylene vinyl acetate (EVA); polycarbonate (PC); polyesters such as polyethylene terephthalate (PET) or PET copolymers (PETG); or polysulphones or polyethersulphones. The polymer may also contain charcoal to reduce odor. Additionally, filters may be coated to enhance hydrophobicity in some embodiments. Polymers may be formed into membranes or sintered (particularly for PVAc, EVA, polyolefin's, and fluoropolymers).

In the example embodiment of FIG. 3, interface 302 and interface 304 are illustrated as separate components that may be bonded together to enclose liquid barrier 306. In other embodiments, dressing connector 208 may be fabricated from a single mold in which interface 302 and interface 304 form a unitary structure. Liquid barrier 306 in this instance may be formed from a sintered polymer, for example, that can be inserted into port 322 of the unitary structure consisting of 302 and 304. This type of assembly may also suit a more common sheet filter welded or glued to a molded carrier that can also be pushed into port 322. Liquid barrier 306 may also be welded or glued directly to a singular unitary structure consisting of 302 and 304.

In an example embodiment of manufacturing a dressing connector such as dressing connector 208, a first interface (such as interface 302) may be formed with a first port (such as port 312), a second port, a first receptacle (such as receptacle 310), and a second receptacle (such as receptacle 308). A first channel, such as channel 318, may be formed from the first port to the first receptacle. A second channel, such as channel 316, may be formed from the second port to the second receptacle. A tube such as tube 206 may be coupled to the first port, such as by bonding the tube to the first port with an adhesive. A second interface (such as interface 304) may be formed with a third port (such as aperture 320) and a fitting (such as fitting 322). The second port and the third port may be aligned and a liquid barrier disposed between the second port and the third port before coupling the first interface to the second interface.

Figure 4:
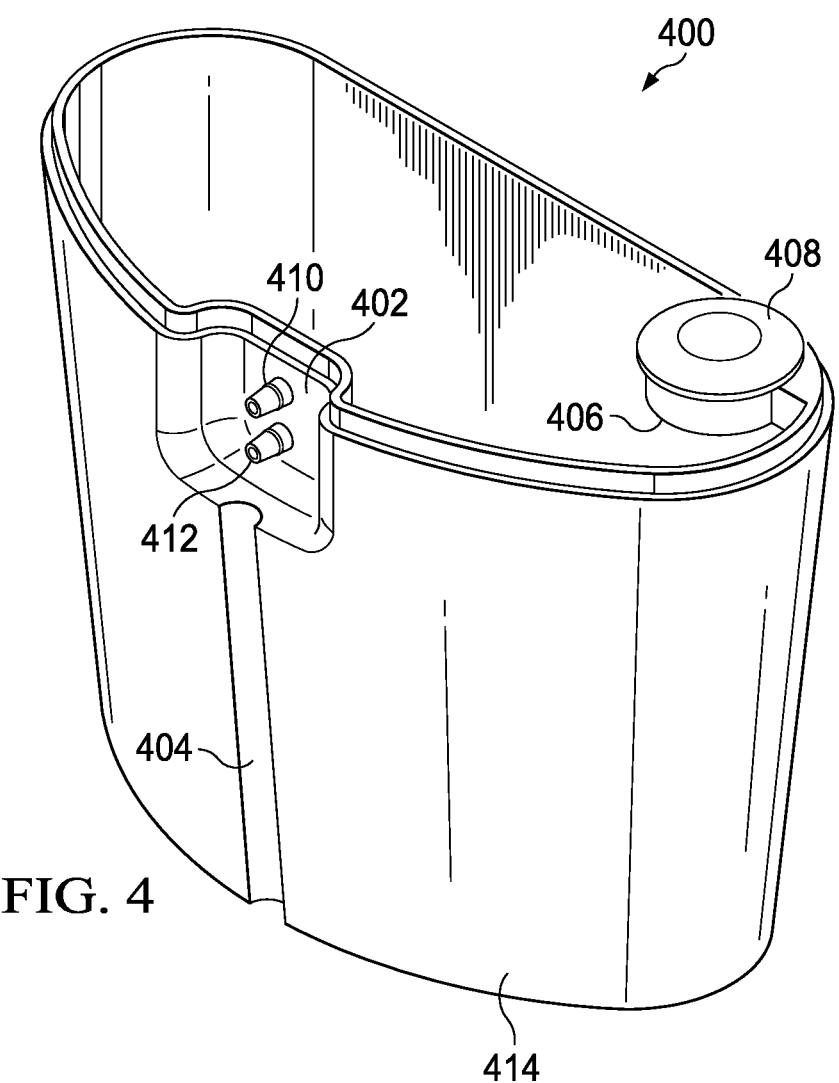
FIG. 4 is perspective view of a container that may be associated with example embodiments of the reduced-pressure therapy system.

FIG. 4 is a perspective view of a container that may be associated with example embodiments of reduced-pressure therapy system 100. In this example embodiment, the container may be a rigid canister 400 that generally includes an interface 402, an alignment recess 404, a drain port 406, and a drain cover 408. Interface 402 may be described as a "connector interface" that can be recessed in the body 414 of rigid canister 400 and adapted for fluidly coupling with a dressing connector, such as interface 302 of dressing connector 208. For example, interface 402 may provide fittings 410-412, which can be adapted for coupling to receptacles 308-310, and may be dimensioned and recessed within body 414 of canister 400 to minimize the profile of dressing connector 208. Similarly, alignment recess 404 may be dimensioned to receive tube 206 to minimize the profile of tube 206. More particularly, in one embodiment, alignment recess 404 may have a depth that is substantially equivalent to an outside diameter of a longitudinal portion of tube 206. In some embodiments, rigid canister 400 may additionally include orientation fittings (not shown) adapted to mate with orientation recesses 314a-314b to facilitate proper orientation of dressing connector 208. In more particular embodiments, fitting 410 may be an outlet fitting adapted to sealingly engage and exhaust fluid flow to an inlet receptacle of a dressing connector, and fitting 412 may be an inlet fitting adapted to sealingly engage and receive fluid flow from a dressing connector, such as dressing connector 208. In the particular example embodiment illustrated in FIG. 4, canister 400 also provides a shoulder 416, a ridge 418 fixed to shoulder 416, and an end surface 418. Shoulder 416 and ridge 418 are adapted to abut a counterpart ridge and shoulder, respectively, on another component, such as a reduced-pressure source. Thus, shoulder 416 and ridge 418 can be used as a structural support for coupling to other components, as well as providing clearance for drain port 406 and drain cover 408 positioned on end surface 418, as shown in FIG. 4.

In one example method of providing reduced-pressure therapy, a dressing may be coupled to a first dressing connector. For example, a dressing may be applied to a tissue site and tube 206 may be coupled to the dressing and to dressing connector 208. Dressing connector 208 may then be coupled to canister 400, such as by pressing receptacles 308-310 onto fittings 410-412, respectively. In some embodiments, orientation recesses 314a-314b may also be aligned with corresponding orientation fittings on canister 400. Canister 400 and dressing connector 208 can then be coupled to reduced-pressure source 210, such that liquid barrier 306 is disposed in the fluid path between canister 400 and reduced-pressure source 210. Tube 206 may be placed in alignment recess 404, and therapy may be initiated (reduced-pressure source 210 may be activated and reduced pressure applied through the dressing, for example). In some embodiments, reduced-pressure therapy system 100 may include a leak detector and can be programmed to activate an alarm or alert if drain cover 408 is not replaced properly or if dressing connector 208 is not properly coupled to reduced-pressure source 210.

Reduced-pressure may be applied and exudates collected from the tissue site in canister 400 until canister 400 is substantially full, the dressing needs changing, or therapy is complete, for example. Exudates may be emptied from canister 400, and dressing connector 208 may be replaced with a second dressing connector having a second (and preferably unused) liquid barrier. For example, the dressing may be removed from the tissue site, and dressing connector 208 may be removed from canister 400. A second dressing can be coupled to the second dressing connector, which can be coupled to canister 400 and reduced-pressure source 210. Dressing connector 208 (with liquid barrier 306) can (and should) be disposed of with the dressing, which encourages regular changes of liquid barrier 306.

These operations are merely illustrative, however, and some of these operations may be consolidated or omitted, where appropriate, and these operations may be modified or changed considerably without departing from the scope of teachings provided herein. In addition, a number of these operations may be executed concurrently with, or in parallel to, one or more additional operations. The sequence of these operations may be altered considerably, as reduced-pressure therapy system 100 provides substantial flexibility.

Figure 5:
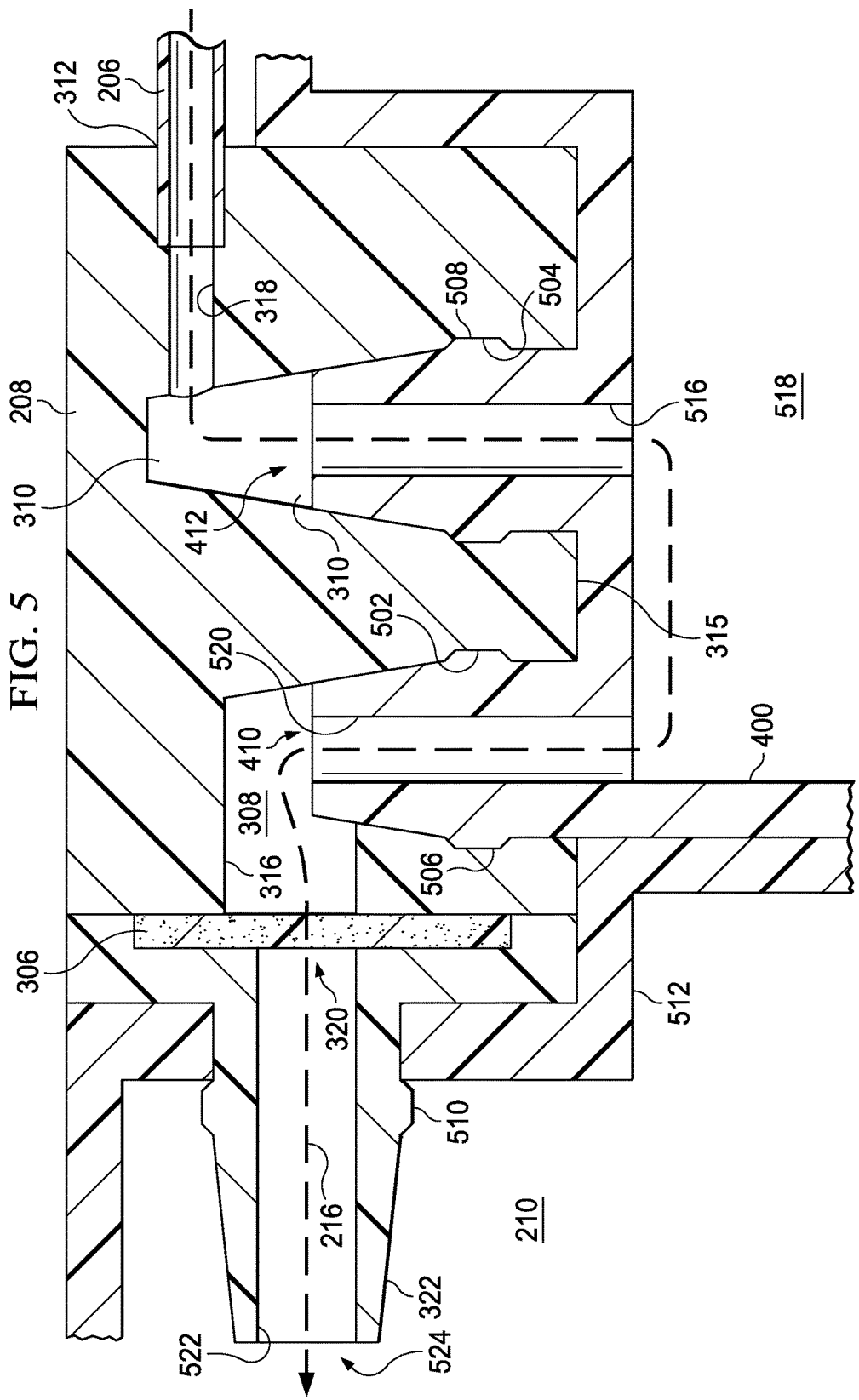
FIG. 5 is a partial cross-sectional view of the dressing connector of FIG. 3 and the container of FIG. 4 illustrating additional details that may be associated with some embodiments of the reduced-pressure therapy system.

FIG. 5 is a partial cross-sectional view of dressing connector 208 and canister 400 illustrating additional details that may be associated with some embodiments of reduced-pressure therapy system 100. Dressing connector 208 is shown engaged with canister 400 in FIG. 5, such that fittings 410-412 are inserted into receptacles 308-310, respectively. In the example embodiment of FIG. 5, receptacles 308-310 and fittings 410-412 are tapered (chamfered) to guide the relative movement between receptacles 308-310 and fittings 410-412. Receptacles 308-310 may also provide recesses 502-504 adapted to engage and retain ridges 506-508 on fittings 410-412. In some embodiments, recesses 502-504 and ridges 506-508 may be annular recesses and ridges. In other example embodiments, ridges 506-508 may be flexible pins or pegs. In some embodiments, only a single pin or peg may be preferable, while in other embodiments several pins or pegs may be annularly spaced (regularly or irregularly) about fittings 410-412. Additionally or alternatively, recesses 502-504 and ridges 506 may be configured to allow dressing connector 208 to engage canister 400 in only one orientation. Recesses 502-504 may be adapted to mate with ridges 506-508 accordingly. Fitting 322 may also provide a chamfered surface and a ridge 510 adapted to engage a receptacle 512, which may be associated with a conduit to or a housing of a reduced-pressure source or other downstream component, for example.

When engaged, as illustrated in the example embodiments of FIG. 5, dressing connector 208 and canister 400 provide fluid path 216 between an upstream component, such as a dressing, and receptacle 512. Fluid path 216 in this example can be generally described as having several parts. For example, a lumen through tube 206 provides a fluid path between the upstream component and port 312, and channel 318 provides a fluid path between port 312 and receptacle 310. A channel 516 through fitting 412, a chamber 518 in canister 400, and a channel 520 through fitting 410 provide a fluid path between receptacle 310 and receptacle 308. Channel 316 and a channel 522 through fitting 322 provide a fluid path between receptacle 308 and an aperture 524 exposed on exterior surface 315. Liquid barrier 306 in this example can be disposed inline, i.e., in fluid path 216, between aperture 317 and aperture 320. The components of dressing connector 208 and canister 400 are preferably adapted to provide an airtight seal when coupled. For example, fittings 410-412 and receptacles 308-310 may be sized to provide a press fit or an interference fit that substantially seals fluid path 216 from external environments.

Figure 6:
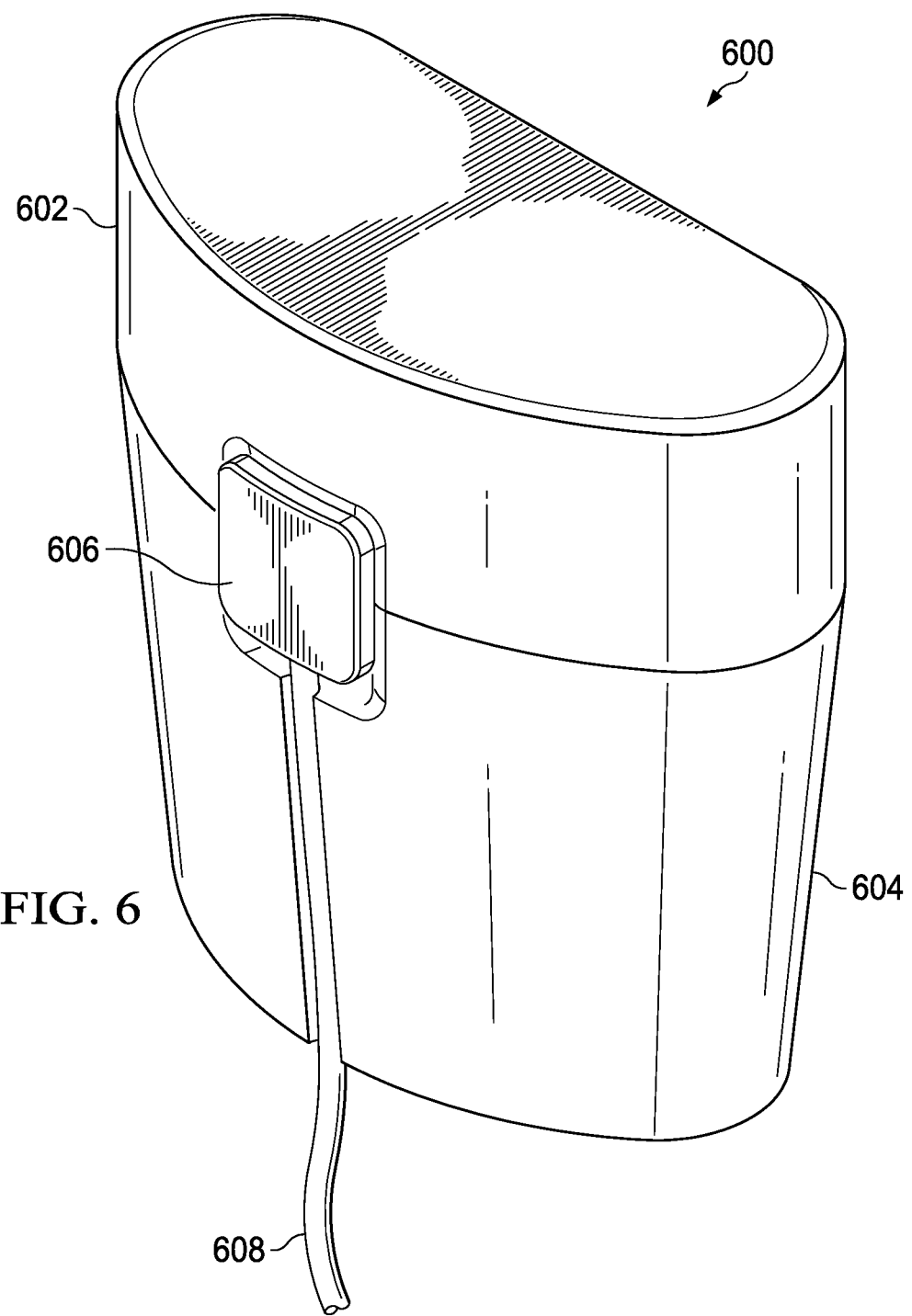
FIG. 6 is a perspective view of another example embodiment of a reduced-pressure therapy system.

FIG. 6 is a perspective view of an example embodiment of a reduced-pressure therapy system 600. This example embodiment illustrates a reduced-pressure source 602 adapted to mate with a canister 604 to provide a convenient system for applying reduced-pressure therapy. A fluid connection between reduced-pressure source 602 and canister 604 may be provided through a dressing connector 606. Moreover, dressing connector 606 may be adapted to fit in a recess of reduced-pressure source 602 and canister 604 to minimize the profile of the assembly. Tubing 608 may similarly be adapted to fit in a recess of canister 604 to minimize the profile of the assembly, as well as provide additional stability of the fluid connection.

Figure 7:
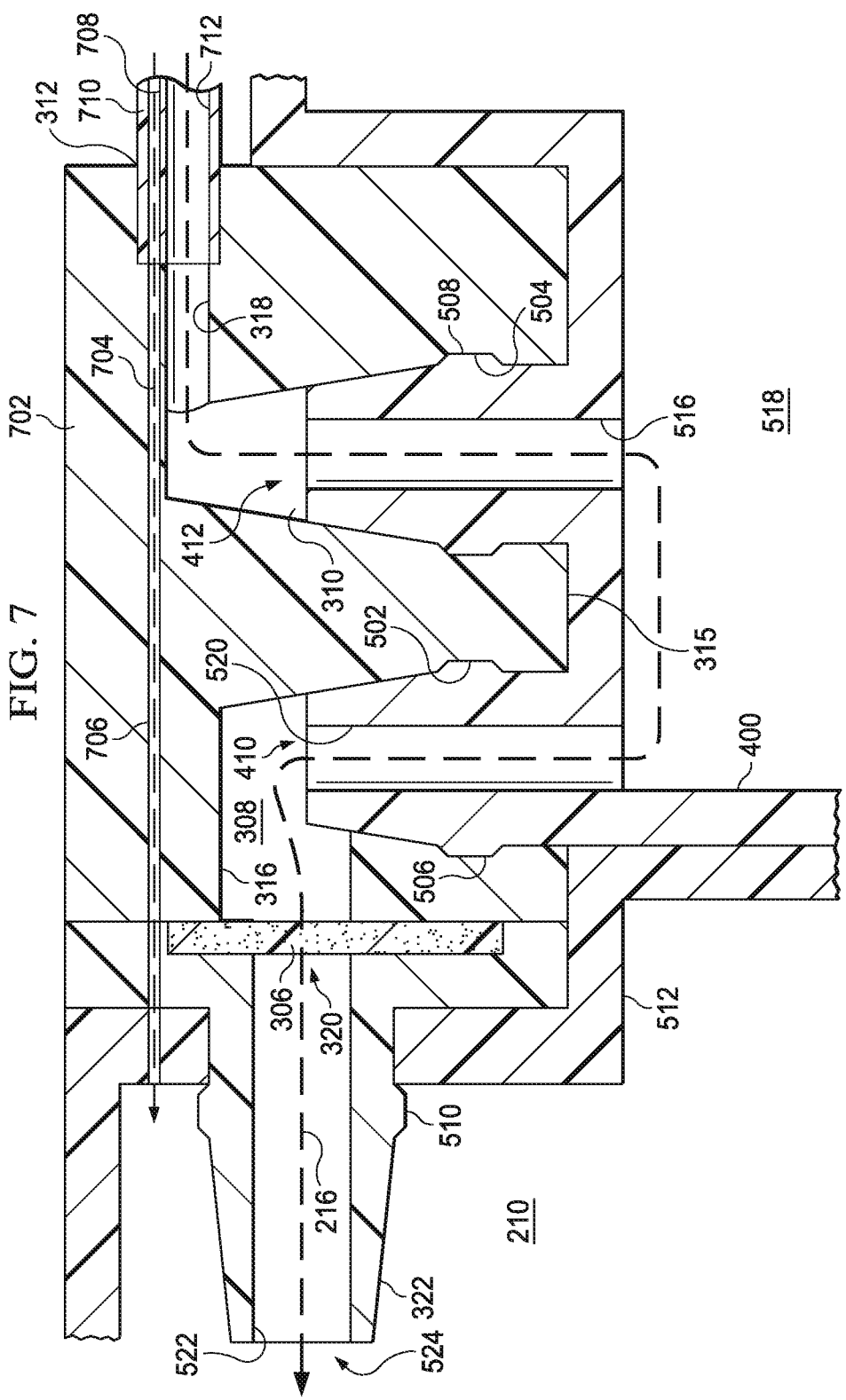
FIG. 7 is a partial cross-sectional view of another example embodiment of a dressing connector that may be associated with the reduced-pressure therapy system.

FIG. 7 is a partial cross-sectional view of another example embodiment of a dressing connector, illustrated as dressing connector 702. Dressing connector 702 is illustrated engaged with a canister, such as canister 400. Dressing connector 702 may be similar to dressing connector 208 in many respects, but may also provide one or more feedback or sensing conduits, such as sensing conduit 704, which can fluidly connect a dressing to a controller or regulator, such as regulator 106. The controller or regulator regulate pressure in the dressing, and may also be adapted to detect improper connections, such as an inadequate connection between the dressing connector and the reduced-pressure source, or an inadequate seal between the drain port and the drain cover. As illustrated, dressing connector 702 can provide fluid path 216 between a downstream component and an upstream component, and also provides another fluid path 706. Fluid path 706 may include, for example, sensing conduit 704 fluidly coupled to a sensing lumen 708 in a multi-lumen tube 710, which can be coupled to a dressing or other upstream component. Fluid path 216 may include a delivery lumen 712 in multi-lumen tube 710 between the upstream component and port 312.

Figure 8B:
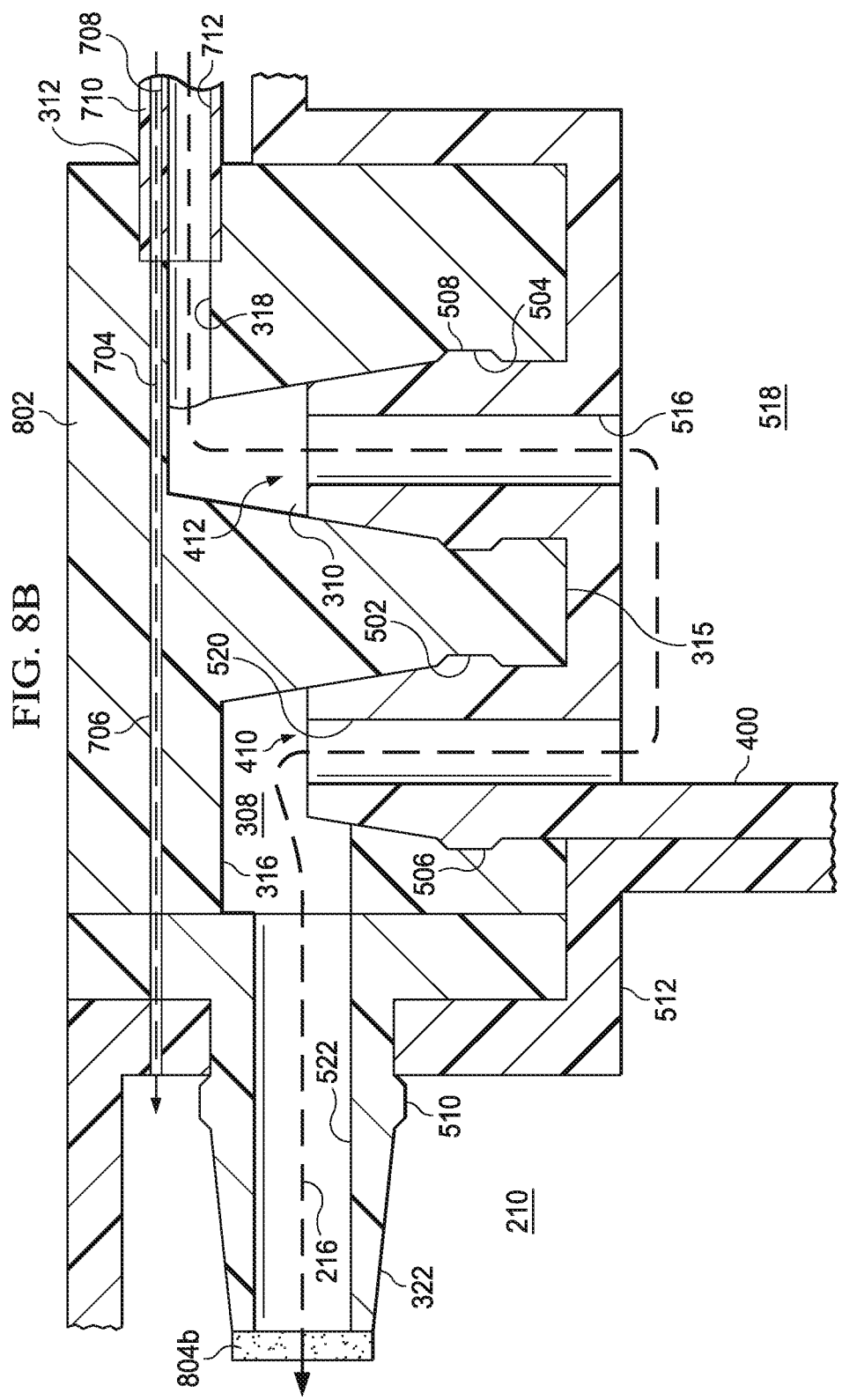

FIGS. 8A-8B are partial cross-sectional views of yet other example embodiments of a dressing connector engaged with a canister. In these examples, a dressing connector 802 is illustrated engaged with a canister, such as canister 400. Dressing connector 802 may be similar to dressing connector 208 and dressing connector 702 in many respects, but is illustrative of an alternative positioning of liquid barrier 804a-804b in fluid path 216. In some embodiments, liquid barrier 804a-804b may be formed from a sintered polymer. Dressing connector 802 in this example may be a unitary structure, and liquid barrier 804a-804b may be welded or glued to port 302. For example, an adhesive may be applied to an exterior surface of liquid barrier 804a, which may be inserted into port 322. Alternatively or additionally, an adhesive may be applied to an exterior surface and/or an interior surface of port 322 before receiving liquid barrier 804a. In other embodiments, liquid barrier 804a may be coupled to port 322 with an interference fit. Adhesive may also be applied to an exterior surface of liquid barrier 804b and/or port 322 to secure liquid barrier 804b in position. Thus, liquid barriers 804a-804b may be disposed in fluid path 216, but may be disposed at least partially external to dressing connector 208, which may reduce part count and manufacturing complexity.

Yet other components may be provided in alternative or additional embodiments. For example, a secondary inline filter may also be provided downstream of the dressing connector. A one-way control valve may be included to control the flow of exudates from the wound, which may be particularly advantageous while emptying the canister to prevent exudates in the tube and air from the surrounding environment from being drawn into the wound. A Vortis pump may additionally be integrated into the dressing connector, which can maintain reduced pressure after drawdown to significantly extend the life of the reduced-pressure therapy system.

In another example embodiment, a drain plug or cover may be integrated with the dressing connector such that the dressing connector must be removed to empty fluid from the canister. The dressing connector may also provide a sacrificial fastener adapted to be broken or rendered inoperable in the process of either fitting the dressing connector to the canister or removing the dressing connector from the canister so that the dressing connector may not be re-used.

The systems and methods described herein may provide significant advantages, some of which have already been mentioned. For example, reduced-pressure therapy system 100 provides a canister that can be re-used, which in turn can lead to significant reduction in cost and environmental impact over the duration of therapy. Moreover, such a canister may be manufactured through a low-cost process such as blow molding, substantially reducing errors in welding filters and potentially leading to yet additional cost savings. Reduced-pressure therapy system may also provide redundant liquid barriers, while promoting regular replacement of the primary liquid barrier without adding a mental burden to therapy.

It should be apparent from the foregoing that an invention having significant advantages has been provided. While shown in only a few forms, the systems and methods illustrated are susceptible to various changes and modifications without departing from the spirit thereof.

We claim:

1. A disposable dressing connector configured to couple a reusable container for collecting exudates to a dressing and to a reduced-pressure source, the dressing connector comprising:
    a first connector and a second connector having a first fluid path between the first connector and the second connector, the first connector configured to connect the first fluid path to the reduced-pressure source and the second connector configured to connect the first fluid path to the reusable container;
    a liquid barrier disposed in the first fluid path; and
    a third connector and a fourth connector having a second fluid path between the third connector and the fourth connector, the third connector configured to connect the second fluid path to the dressing and the fourth connector configured to connect the second fluid path to the reusable container;
    wherein the first fluid path and the second fluid path are exposed to an exterior surface of the dressing connector.

2. The dressing connector of claim 1, wherein:
    the first connector is a fitting;
    the second connector is a first receptacle;
    the third connector is a port; and
    the fourth connector is a second receptacle.

3. The dressing connector of claim 1, further comprising a tube bonded to the third connector.

4. The dressing connector of claim 3, wherein the tube comprises a delivery lumen and a sensing lumen, and further comprising a third fluid path adapted for fluidly coupling with the sensing lumen.

5. The dressing connector of claim 1, wherein the liquid barrier is a filter.

6. The dressing connector of claim 1, wherein the liquid barrier comprises a hydrophobic bacterial filter.

7. The dressing connector of claim 1, wherein the liquid barrier comprises a gel-blocking sintered polymer filter.

8. The dressing connector of claim 1, wherein the liquid barrier comprises a charcoal filter.

9. The dressing connector of claim 1, wherein the first connector is a tapered fitting.

10. The dressing connector of claim 1, wherein the second connector and the fourth connector each comprises a cavity exposed to the exterior surface.

11. The dressing connector of claim 1, wherein the second connector and the fourth connector each comprises a tapered cavity exposed to the exterior surface.

12. The dressing connector of claim 1, wherein the second connector and the fourth connector each comprises a recess within a cavity adapted to engage a ridge on a container fitting.

13. The dressing connector of claim 1, wherein the second connector and the fourth connector each comprises an annular recess adapted to engage a ridge on a container fitting.

14. The dressing connector of claim 1, wherein the first fluid path comprises: a channel through the first connector; and a port exposing the channel to the exterior surface.

15. The dressing connector of claim 1, wherein the first connector comprises a ridge adapted to engage a downstream component.

16. The dressing connector of claim 1, further comprising an orientation recess adjacent to the second connector and the fourth connector.

17. The dressing connector of claim 1, further comprising a one-way valve in the second fluid path.

18. The dressing connector of claim 1, wherein the liquid barrier is disposed at least partially external to both the first connector and the exterior surface of the dressing connector.

19. A disposable dressing connector configured to couple a reusable container for collecting exudates to a dressing and to a reduced-pressure source, the dressing connector comprising:
    a fitting fluidly coupled to a first receptacle through an inline liquid barrier, the fitting configured to connect to the reduced-pressure source and the first receptacle configured to connect to the reusable container;
    a port fluidly coupled to a second receptacle, the port configured to connect to the dressing and the second receptacle configured to connect to the reusable container; and
    a tube fluidly coupled to the port;
    wherein the first receptacle and the second receptacle each comprises a cavity exposed to an exterior surface adapted to engage a container fitting.

20. The dressing connector of claim 19, wherein:
    the fitting comprises a male fitting and an annular ridge adapted to engage the downstream component; and
    each cavity comprises an annular recess adapted to engage the container fitting.

21. The dressing connector of claim 1, wherein at least two of the first connector, the second connector, the third connector, or the fourth connector extend from the exterior surface of the dressing connector.

22. The dressing connector of claim 1, wherein:
    the dressing connector forms a single piece dressing connector removably coupled to a container with a container fitting coupled to at least one of the second connector or the fourth connector;
    the first connector, the second connector, the third connector, and the fourth connector are separate; and
    the exterior surface of the single piece dressing connector is the exterior surface of the dressing connector.

* * * * *